(12) United States Patent
Kasuya (10) Patent No.: US 8,170,175 B2
(45) Date of Patent: May 1, 2012

(54) X-RAY CT APPARATUS AND A METHOD FOR DETECTING MAGNETIC POLE POSITION THEREOF

(75) Inventor: Yuichi Kasuya, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 156 days.

(21) Appl. No.: 12/801,183

(22) Filed: May 26, 2010

(65) Prior Publication Data

US 2010/0303197 A1    Dec. 2, 2010

(30) Foreign Application Priority Data

May 26, 2009    (JP) ............................. P2009-126924

(51) Int. Cl.
*A61B 6/03*    (2006.01)
(52) U.S. Cl. ............................................ 378/15
(58) Field of Classification Search ................ 378/4, 15, 378/207
See application file for complete search history.

(56) References Cited

U.S. PATENT DOCUMENTS

| 6,553,091 | B2 | 4/2003 | Takanashi et al. | |
|---|---|---|---|---|
| 7,283,607 | B2 * | 10/2007 | Sommer | 378/15 |
| 7,760,850 | B2 * | 7/2010 | Kasuya | 378/15 |
| 2007/0274436 | A1 * | 11/2007 | Harada et al. | 378/15 |

FOREIGN PATENT DOCUMENTS

JP    2002-78703    3/2002

* cited by examiner

*Primary Examiner* — Irakli Kiknadze
(74) *Attorney, Agent, or Firm* — Oblon, Spivak, McClelland, Maier & Neustadt, L.L.P.

(57) ABSTRACT

An X-ray CT apparatus includes a fixed gantry having a plurality of stator coils arranged in a circle and mounted on the fixed gantry. A ring-shaped rotation frame of the CT apparatus includes a plurality of rotor magnets facing the plurality of stator coils. The CT apparatus further has an X-ray tube and an X-ray detector situated on the rotation frame to face each other and a supporting unit configured to provide non-contact support of the rotation frame on the fixed gantry. A magnetic pole detection unit of the apparatus is configured to detect a magnetic pole position of the rotor magnet at a start-up time of the plurality of stator coils and a brake mechanism of the apparatus is configured to apply a brake load to the rotation frame when detecting the magnetic pole position and to remove the brake load after detecting the magnetic pole position.

12 Claims, 9 Drawing Sheets

X-RAY CT APPARATUS AND A METHOD FOR DETECTING MAGNETIC POLE POSITION THEREOF

CROSS-REFERENCE TO RELATED APPLICATIONS

This application claims priority under 35 U.S.C. §119(a) from, and the benefit of, Japanese Patent Application No. 2009-126924, filed on May 26, 2009 the contents of which are expressly incorporated herein by reference in their entirety.

BACKGROUND

A. Field

Embodiments described herein relate generally to an X-ray computer tomography (CT) apparatus and a method for detecting a magnetic pole position thereof, and more particularly, to an X-ray CT apparatus having a direct drive motor driving mechanism for rotating a gantry frame and a method for detecting a magnetic pole position of the X-ray CT apparatus at a starting-up time of the gantry frame.

B. Background

An X-ray CT apparatus, widely used in medical and industrial fields, acquires projection data for reconstructing tomography images of an object by irradiating radiation beams around the object. More particularly, the X-ray CT apparatus acquires projection data by rotating an X-ray tube and an X-ray detection unit around the object in one direction, where the X-ray tube and the X-ray detection unit are situated on a ring-shaped rotation frame (gantry rotation unit) in a gantry so as to face each other.

Recently, a high-speed and a high-functioning X-ray CT apparatus has been developed, wherein the rotation frame is rotated at a high speed to acquire projection data at a high speed. In order to rotate the rotation frame at a high speed, the power supply and the signal transmissions and receptions between the rotation frame and a fixed gantry supporting the rotation frame are performed through a slip ring or an optical transmission and the rotation power of a motor situated on the fixed gantry is transferred to the rotation frame through the gears and belts of the motor. However, such a rotation driving power transferring system generates relatively large mechanical vibrations and operation sounds that may cause discomfort to a patient or an operator.

Recently, a high speed X-ray CT apparatus was proposed wherein quiet sound imaging is achieved without using gears and belts. Instead, the apparatus uses a direct drive motor (hereinafter, simply referred to as "DD motor") driving system that transfers the rotation power to the rotation frame by non-contacting technology.

In the DD motor driving system, the non-contacting rotation power transmission is performed between the windings on the rotation frame and the magnets on the gantry fixing unit. More specifically, the rotation frame is directly rotationally driven as a non-contacting rotor member of a repulsion motor by repulsions between the magnetic fluxes generated by supplying a current to the windings of the rotation frame and the magnetic fluxes from the magnets on the gantry fixing unit. The repulsion DD motor driving circuit may also be constructed by situating the windings on the gantry fixing unit so as to act repulsively to the magnets on the rotation frame.

At a start-up time of a DD motor, where the rotation frame is constructed as a non-contacting rotor member, a rotation direction of the rotation frame and switching timings of the magnetic poles can be determined by controlling pulse signals supplied to the windings. The pulse signals are supplied in accordance with both a center-to-center distance between a center position of the winding and a center position of the fixed magnet, and the magnetic pole (N-pole, S-pole) of the rotor magnet. Usually, the magnetic pole position at the starting-up time of the DD motor is determined by exciting the gantry rotation frame—e.g., by supplying currents to the windings of the rotation unit during a very short time period—and estimating the magnetic pole position at starting-up time of the DD motor based on the time period between a resulting vibration start-up time and a vibration stop time.

In the conventionally proposed quiet X-ray CT apparatus of the DD motor driving system, the fixed gantry supports the rotation frame through ball bearings, and the fixed gantry supplies rotation power to the rotation frame through a slip ring between the rotation frame and the fixed gantry. As a result, when the DD motor is started up, the slip ring and the ball-bearings create friction resistances of the rotation frame against the fixed gantry. Thus, when the rotation frame is excited during a very short time, the vibration of the rotation frame converges, or gradually focuses, and stops after a prescribed time period due to the friction resistances. Accordingly, it is possible to estimate the magnetic pole position based on the time period between the start of vibration and the end of the vibration.

Nevertheless, a more silent imaging of the X-ray CT apparatus has persistently been required. One approach replaces the power supply from the fixed gantry to the rotation frame through a slip ring with a non-contacting power supply and the support of the rotation frame on the fixed gantry through ball-bearings with an air bearing support.

However, supporting the rotation frame by the fixed gantry using air bearings makes it difficult to easily estimate the magnetic pole position by exciting the rotation frame during a short time at a start-up of the DD motor because the vibration of the rotation frame cannot be easily converged and stopped in a short time due to the much lower friction resistances of the rotation frame against the fixed gantry than in contacting supports. Thus, it becomes difficult to easily estimate the magnetic pole position at the starting-up time of the DD motor in a short time. This generates a drawback that it takes a long time until acquisition of projection data can be started.

BRIEF DESCRIPTION OF THE DRAWINGS

The accompanying drawings, which are incorporated in and constitute part of this specification, illustrate various non-limiting exemplary embodiments and/or features of the invention and, together with the description, serve to explain the invention. Where possible, the same reference number will be used throughout the drawings to describe the same or like parts. In the drawings.

DETAILED DESCRIPTION

According to certain exemplary embodiments, an X-ray CT apparatus includes a fixed gantry having a plurality of stator coils arranged in a circle and mounted on the fixed gantry. A ring-shaped rotation frame of the CT apparatus includes a plurality of rotor magnets facing the plurality of stator coils. The CT apparatus further has an X-ray tube and an X-ray detector situated on the rotation frame to face each other and a supporting unit configured to provide non-contact support of the rotation frame on the fixed gantry. A magnetic pole detection unit of the apparatus is configured to detect a magnetic pole position of the rotor magnet at a start-up time of the plurality of stator coils and a brake mechanism of the apparatus is configured to apply a brake load to the rotation frame when detecting the magnetic pole position and to remove the brake load after detecting the magnetic pole position.

According to another embodiment, a method is provided for detecting a magnetic pole position of a direct drive (DD) motor type X-ray CT apparatus that includes a fixed gantry configured to mount a plurality of circularly-provided stator coils, and a ring-shaped rotation frame configured to provide a plurality of rotor magnets facing the plurality of stator coils. The method includes activating a magnetic pole position detection function by a prescribed operation to a control unit of the apparatus at a start-up time and, based on the activation of the magnetic pole position detection function, applying a current to the plurality of stator coils by supplying a drive current to a driving circuit for the DD motor during a short time. The method further includes operating a brake system so as to prohibit the rotation of the rotation frame by the control unit and detecting a magnetic pole position of the rotor magnet based on a number of encode pulses_between a vibration start-up time and a vibration stop time, where the vibration is due to the operation of the brake system.

In another embodiment, an X-ray CT apparatus has a fixed gantry configured to mount a plurality of circularly-provided stator coils and a ring-shaped rotation frame configured to provide a plurality of rotor magnets facing the plurality of stator coils. The apparatus also has an X-ray tube and an X-ray detector situated on the rotation frame so as to face each other and a supporting means for achieving a non-contact support of the rotation frame on the fixed gantry. The apparatus further includes magnetic pole detection means and braking means. The magnetic pole detection means is for detecting a magnetic pole position of the rotor magnet at a start-up time of the plurality of stator coils and the braking means is for applying a brake load to the rotation frame when detecting the magnetic pole position and for removing the brake load after detecting the magnetic pole position.

According to one embodiment, an X-ray CT apparatus having a DD motor driving system in which a rotation frame is supported on a fixed gantry through a non-contacting supporting unit, such as air bearings, can easily detect a magnetic pole position at a starting-up time. As a result, it becomes possible to quickly start acquisition of projection data by steadily driving the DD motor.

Figure 1:
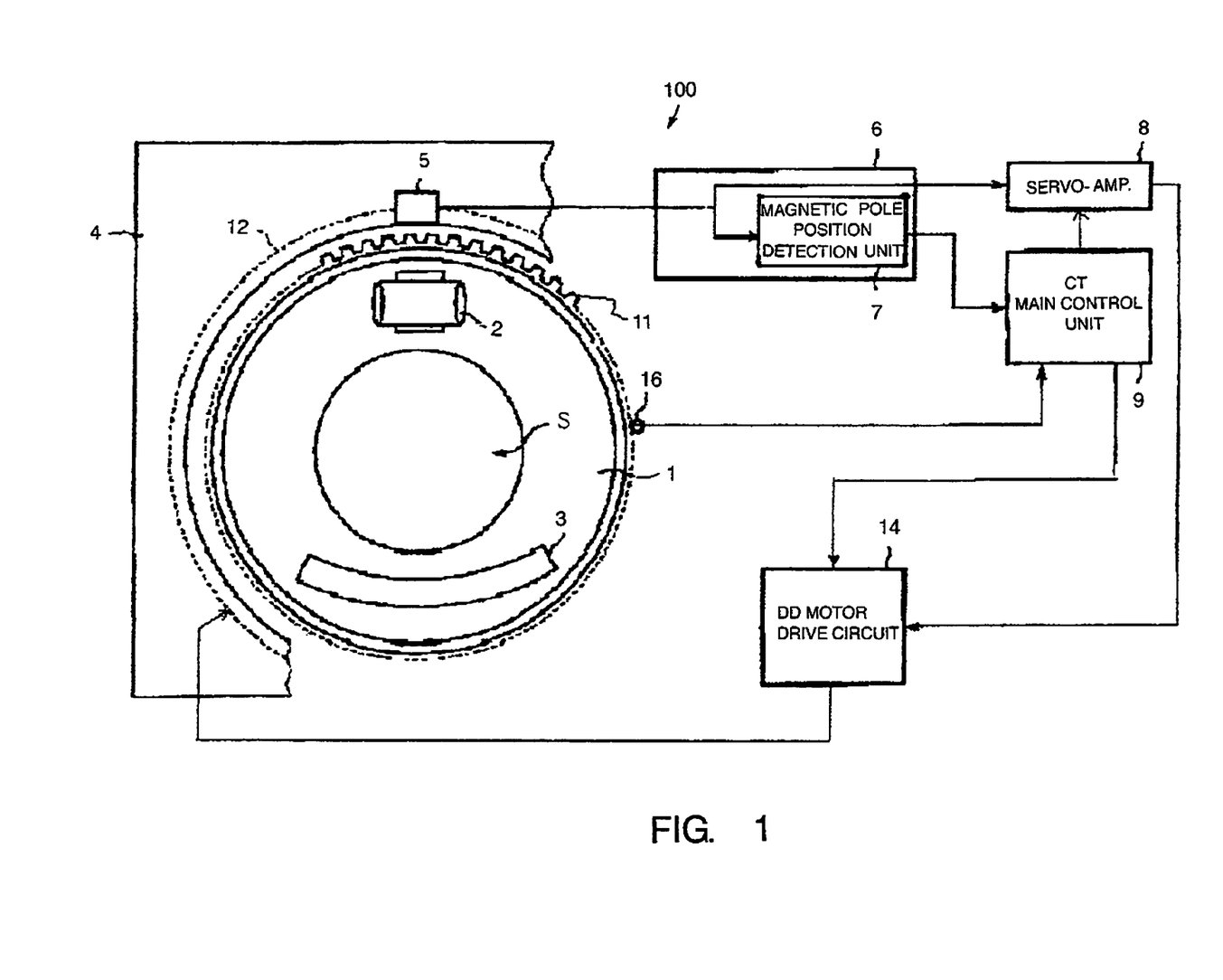
FIG. 1 is a block diagram illustrating a construction of one embodiment of an X-ray CT apparatus.

FIG. 1 illustrates one construction of a non-limiting embodiment of an X-ray CT apparatus 100. The X-ray CT apparatus 100 includes a circular (ring-shaped) rotation frame 1 in a fixed gantry 4. The rotation frame 1 includes a cylindrical space S at a center portion, and an X-ray tube 2 and an X-ray detector 3 are situated on the rotation frame 1 so as to face each other through the space S. The rotation frame 1 is supported by a non-contact supporting unit, i.e., air bearings, on the fixed gantry 4 so as to rotate while keeping a small gap between them. The rotation frame 1 is driven by a DD motor driving system that includes rotor magnets 11 and stator coils 12. On the fixed gantry 4, a magnetic sensor 5 and a reference position sensor 16 are provided. As will be explained later, the magnetic sensor 5 detects flux changes in accordance with the rotation of the rotor magnets. Reference position sensor 16 detects a reference position and a rotation speed of the rotation frame 1.

Figure 2:
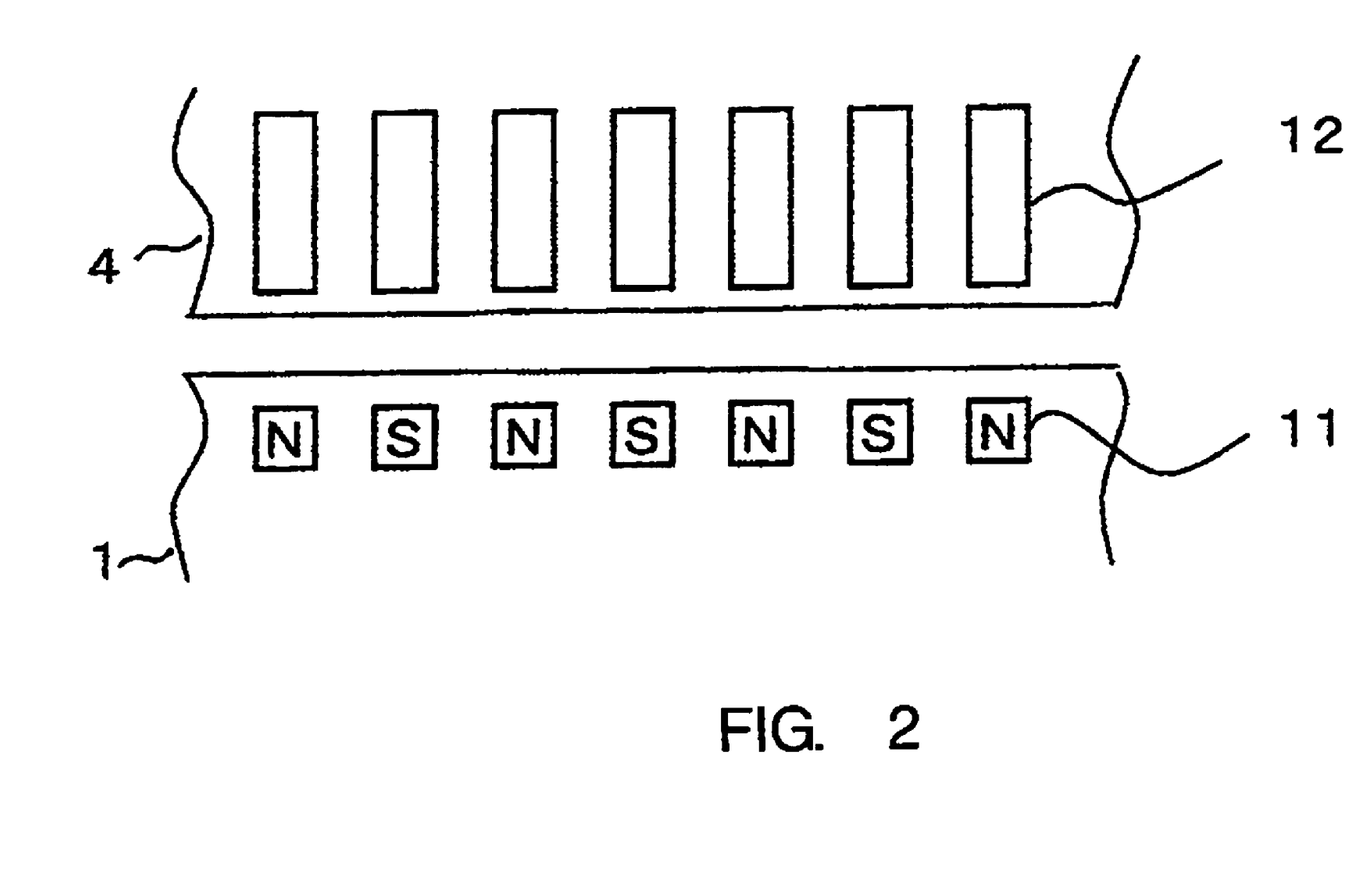
FIG. 2 illustrates a portion of an arrangement of rotor magnets and stator coils for constructing the DD motor in the X-ray CT apparatus shown in FIG. 1.

FIG. 2 illustrates a partial arrangement of rotor magnets 11 and stator coils 12 for constructing a DD motor. As shown in FIG. 2, a plurality of rotor magnets 11 is provided along the circular rotation frame 1 so that the plurality of north (N) poles and south (S) poles is alternately arranged. On the fixed gantry 4, a plurality of stator coils (windings) 12 is provided so as to face each of the plurality of rotor magnets 11. In accordance with the rotation of the rotor magnets 11 on the rotation frame 1, flux changes are detected by the magnetic sensor 5 provided on the fixed gantry 4.

Referring to FIG. 1, the X-ray CT apparatus 100 further includes a signal processing unit 6, a magnetic pole position detection unit 7, a servo amplifier 8, a DD motor driving circuit 14 and a CT main control unit 9. The signal processing unit 6 generates pulse signals by processing the detection signals from the magnetic sensor 5. The magnetic pole position detection unit 7 includes a memory for identifying a magnetic pole position based on the detection signals from the sensor 5. The servo amplifier 8 supplies driving signals to the DD motor based on the pulse signals from the signal processing unit 6. By receiving the driving signals from the servo amplifier 8, the DD motor driving circuit 14 supplies driving currents to the stator coils 12 of the DD motor. The CT main control unit 9 controls the overall operation of the X-ray CT apparatus.

By supplying currents to the stator coils 12 of the DD motor from the DD motor driving circuit 14, repulsion occurs between the magnetic flux from the rotor magnet 11 and the magnetic flux from the stator coil 12. Consequently, it becomes possible to directly drive the rotation frame 1 as a motor rotor by controlling the current supply to the stator coil 12. The rotor magnet 11 also rotates with rotation frame 1. Accordingly, the flux changes due to the rotating of the rotor magnet 11 can be detected by the magnetic sensor 5, which continuously transmits encode pulses during the detecting time period of the flux changes.

The DD motor driving circuit 14 supplies currents for driving the rotation frame 1 to the stator coils 12 of the DD motor. The DD motor driving circuit 14 is controlled by the control signals from a control system comprised of the magnetic sensor 5, the signal processing unit 6, the magnetic pole position detection unit 7, the servo amplifier 8 and the CT main control unit 9.

Figure 3:
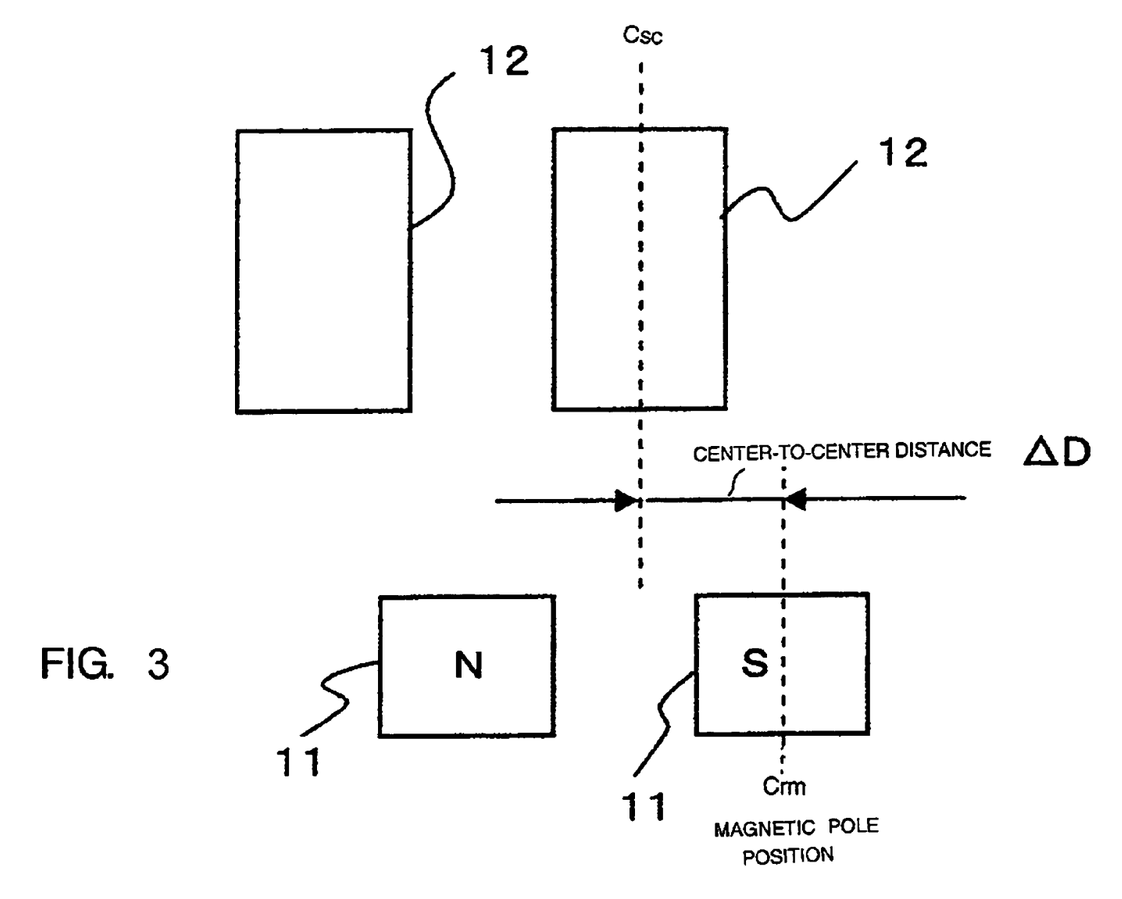
FIG. 3 depicts a magnetic pole position of the DD motor shown in FIG. 2.

FIG. 3 illustrates detection of a magnetic pole position at a starting-up time of the DD motor. As depicted in FIG. 3, the magnetic pole position is defined in terms of a center-to-center distance ΔD between a center Csc of each stator coil 12 and a center Crm of each rotor magnet 11, and a magnetic pole of the rotor magnet 11. Since the magnetic pole position is determined by resident properties of the rotation frame 1, such as a distortion and a gravity center, the magnetic pole position reappears at the same position in an excitation stopped state of the stator coil 12. Consequently, in accordance with the center-to-center distance ΔD at a starting-up time of the DD motor, a time period until a first polarity inversion from a start of a power supply is adjusted by adjusting a drive current supplied to the stator coil 12 from the servo amplifier 8. Thus, when the rotation frame 1 is excited by supplying a current to the stator coil 12 during a very short time in accordance with the center-to-center distance ΔD, the vibration of the rotation frame 1 is stopped at a certain time. The time from the excitation to the stopping of the rotation frame is the convergence time, which is used to estimate the magnetic pole position. Accordingly, correspondence relations between a preliminarily measured plurality of convergence times and a plurality of magnetic pole positions are stored in a memory of the magnetic pole position detection unit 7.

Figure 4:
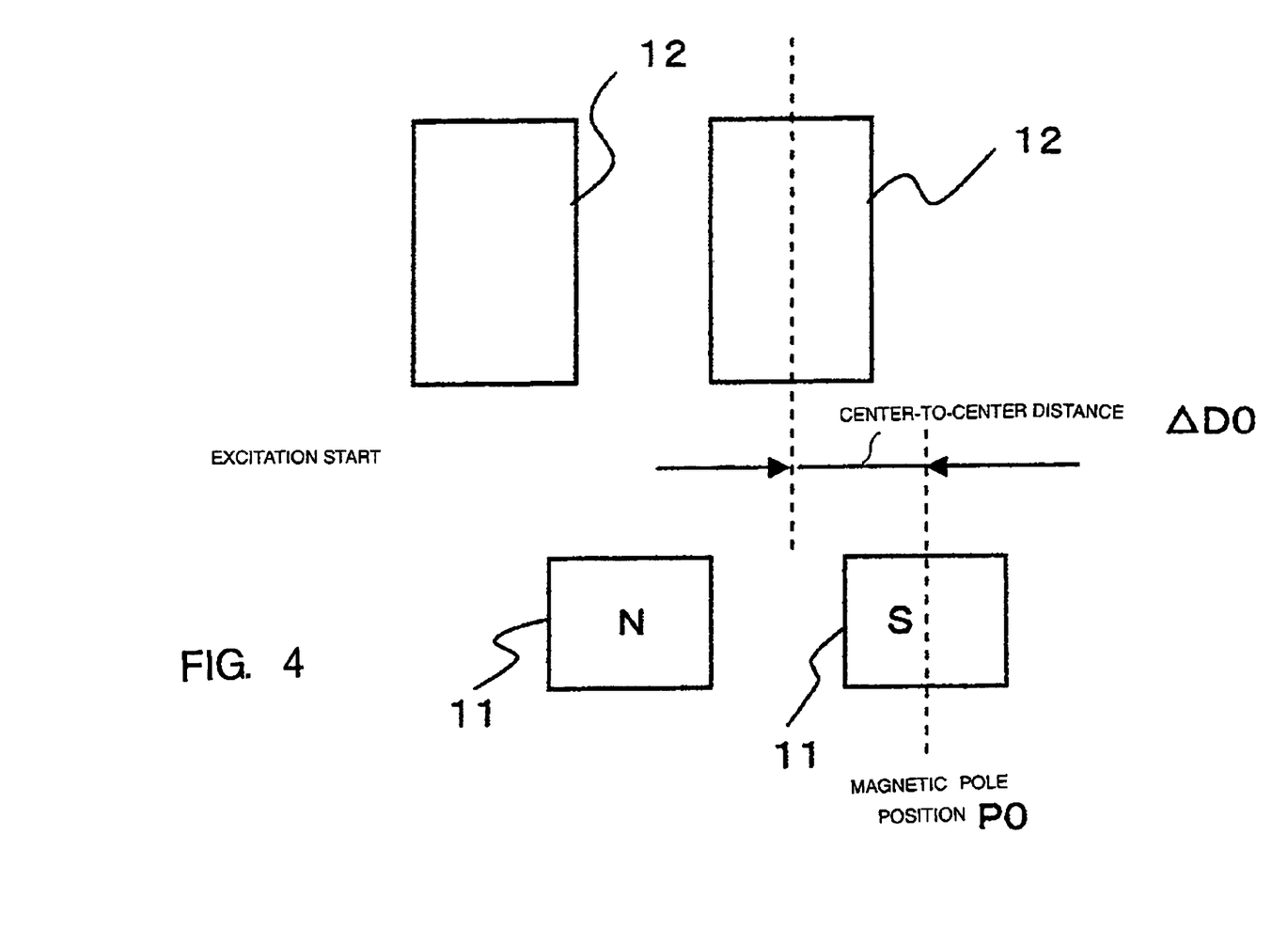
FIG. 4 illustrates a status of the rotor magnet and the stator coil in the DD motor at a start-up time of excitation.

FIG. 4 illustrates a state of the rotor magnet 11 and the stator coil 12 at an excitation start-up time of the DD motor. At a starting-up time of the DD motor, a user starts a magnetic pole position detection operation by performing a prescribed operation to the CT main control unit 9. As illustrated in FIG. 4, in an initial state of the magnetic pole position detection operation, the magnetic pole position is at a center position P0 of the rotor magnet 11, and a center-to-center distance between the stator coil 12 and the rotor magnet 11 is ΔD0. In this state, the CT main control unit 9 passes a control signal to the servo amplifier 8 to supply a current having a prescribed polarity and amplitude during a very short time to the stator coil 12.

Figure 5:
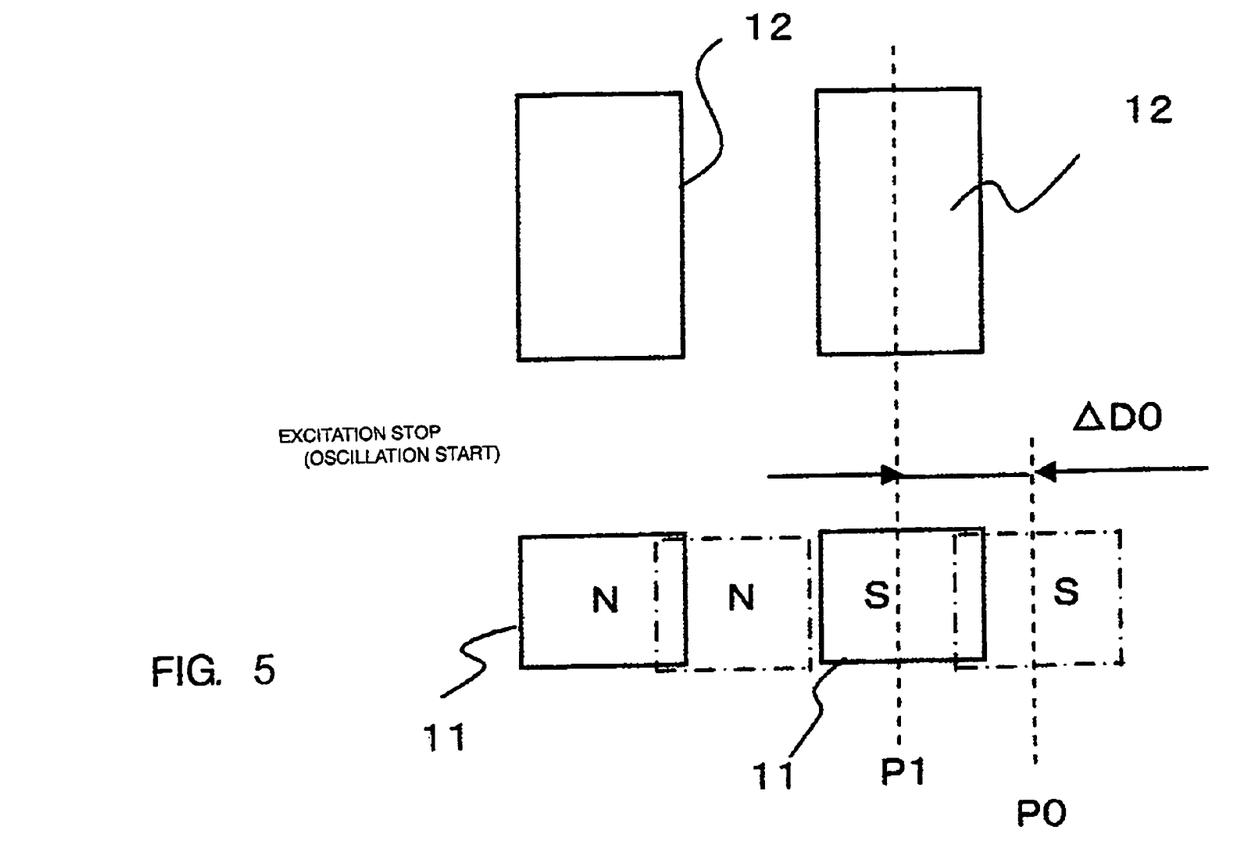
FIG. 5 illustrates a status of the rotor magnet and the stator coil in the DD motor at a stop time of excitation.

As illustrated in FIG. 5, when the stator coil 12 is excited by supplying the current, repulsions occur between the magnetic fluxes generated from the stator coil 12 and the magnetic fluxes from the rotor magnet 11, causing the magnetic pole position to move from an origin position P0 to a first position P1. Thus, by moving the magnetic pole position, the position of the rotor magnet 11 with respect to the stator coil 12 is also moved. As a result, the rotation frame 1 starts rotation. At that moment, the current supplied to the stator coil 12 is suddenly cut off, causing the rotation frame 1 to begin vibrating (oscillating) at that position. The vibration of the rotation frame 1 gradually converges.

Figure 6:
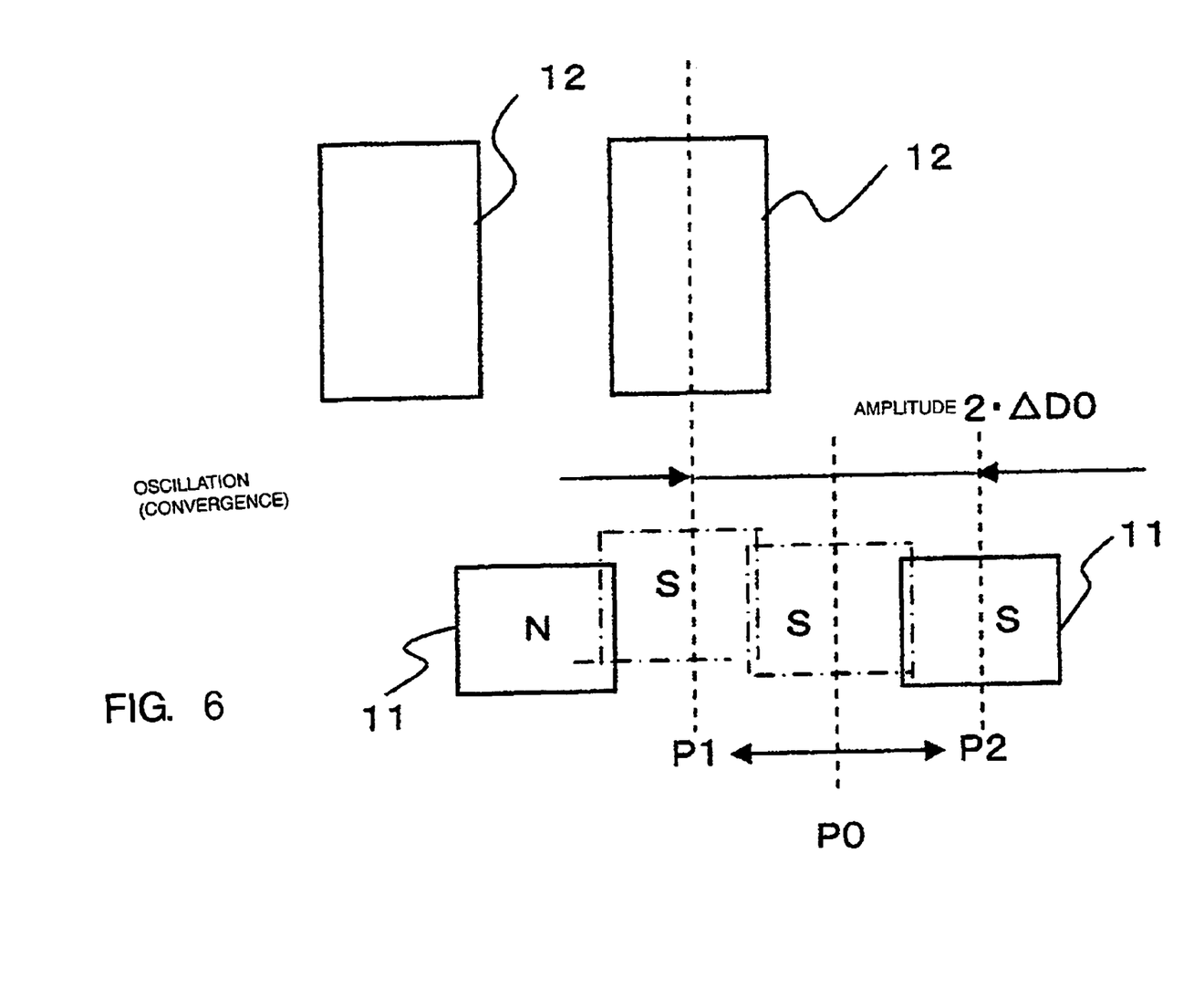
FIG. 6 illustrates a status of the rotor magnet and the stator coil during vibration of the DD motor.
Figure 7:
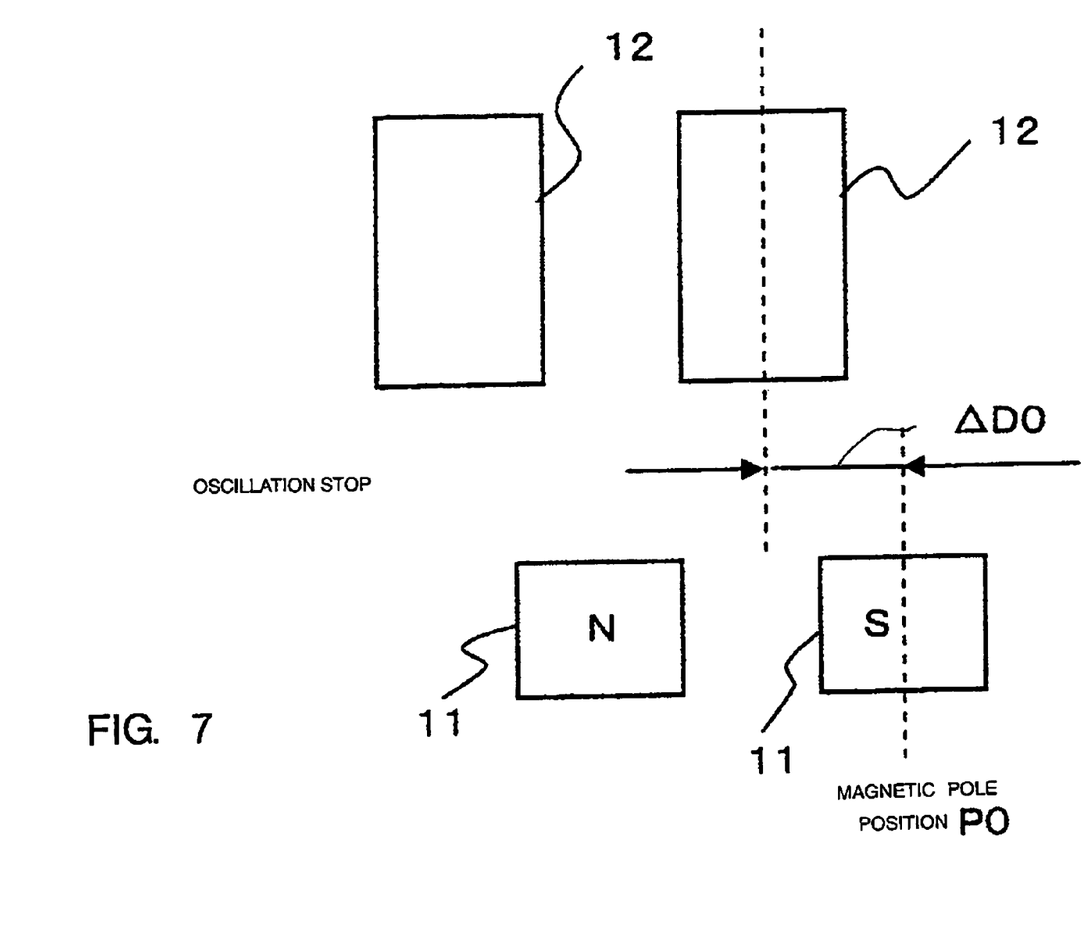
FIG. 7 illustrates a status of the rotor magnet and the stator coil at a vibration stop time of the DD motor.

FIG. 6 illustrates the moving status of the magnetic pole position between the positions P1 and P2 when the rotation frame 1 is converged after a start of the vibration. The vibration is gradually converged and is finally stopped. As illustrated in FIG. 7, when the vibration is stopped, the rotation frame 1 is stopped at the initial state of magnetic pole position P0.

Referencing FIG. 1, the magnetic pole position detection unit 7 measures a time period from the vibration start due to the sudden shutoff of the current supply to the stator coil 12, to the stopping of the rotation frame 1 due to the convergence of the vibration. The time measurement is performed by counting the number of encode pulses supplied by the magnetic sensor 5. Based on the convergence time corresponding to the number of encode pulses, a magnetic pole position is determined by reading out the correspondence relation between the convergence time and the magnetic pole position from the memory. By detecting the magnetic pole position, excitation conditions are determined. The DD motor is started up under the determined excitation conditions by supplying a start-up signal to the DD motor driving circuit 14 from the servo amplifier 8.

The servo amplifier 8 supplies driving signals to the DD motor driving circuit 14 in accordance with control signals from the CT main control unit 9. The rotation frame 1 is rotated by supplying drive currents from the DD motor driving circuit 14 to the stator coil 12 of the DD motor based on the driving signals from the servo amplifier 8.

The DD motor driving circuit 14 also receives rotation mode set-up instructions, such as a scan start instruction or a scan stop instruction and a rotation speed instruction, from the CT main control unit 9. Accordingly, the rotation frame 1 is rotated at the rotation speed specified by the CT main control unit 9. The reference position—i.e., the magnetic pole position before rotation—and the rotation speed of the rotation frame 1 are detected by the reference position sensor 16 situated on the fixed gantry 4 and are supplied to the CT main control unit 9. Based on both the receipt time of the reference position and the rotation speed of the rotation frame 1, the CT main control unit 9 generates position signals by calculating a rotation position of the rotation frame 1.

In the DD motor driving type X-ray CT apparatus wherein the rotation frame 1 is supported on the fixed gantry 4 through the air bearings, the friction resistances of the rotation frame 1 to the fixed gantry 4 become very low. As a result, even when the rotation frame 1 is excited during a very short time period at start-up of the DD motor, the vibration resulting from a sudden stop of the driving signal cannot be converged for a long time and the magnetic pole position cannot be easily estimated.

Figure 8:
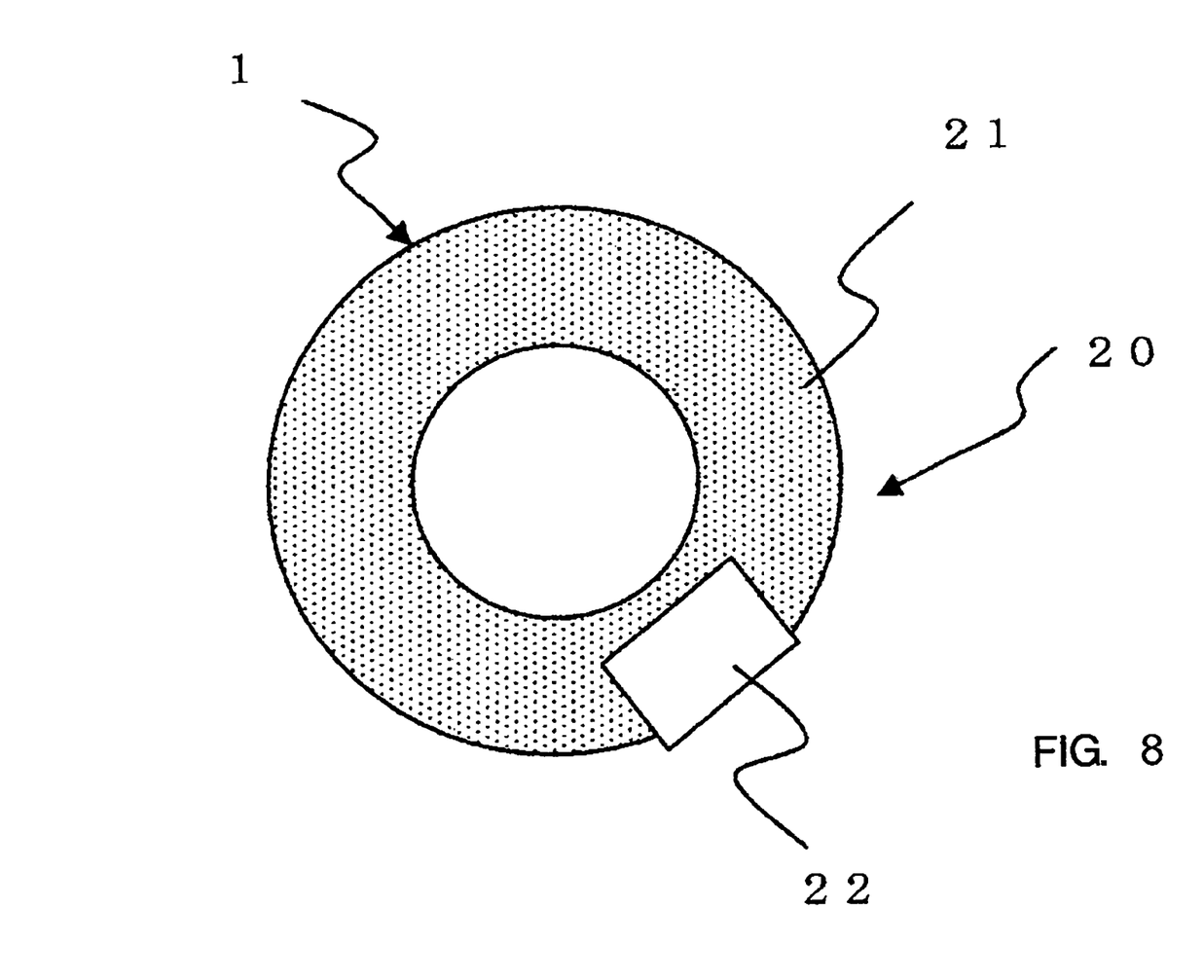
FIG. 8 illustrates one embodiment of a brake mechanism used in an X-ray CT apparatus consistent with the embodiment of FIG. 1.

According to a non-limiting exemplary embodiment, a brake mechanism is used to more rapidly stop the vibration of the rotation frame 1. FIG. 8 illustrates an exemplary embodiment of a brake mechanism 20 for stopping the vibration of the rotation frame 1. The brake mechanism 20 applies a brake load to the rotation frame 1 and releases the brake load from the rotation frame 1 in order to detect a magnetic pole position at a start-up time of the DD motor drive type X-ray CT apparatus. As illustrated in FIG. 8, the brake mechanism 20 is comprised of, for instance, a friction plate 21 and a brake pad 22.

The friction plate 21, for instance, has a circular shape and is attached on a surface of the rotation frame 1. The brake pad 22 is situated on the fixed gantry 4 so as to partially confront the friction plate 21. The brake pad 22 is moved so as to firmly push on the friction plate 21 by applying current, and it separates from the friction plate 21 by stopping the current supply. Thus, since the brake pad 22 is moved so as to firmly contact the friction plate 21 by applying current, the friction resistances of the rotation frame 1 are increased and rotation of the rotation frame 1 is prohibited. When application of current is stopped, the brake pad 22 releases, thereby removing the friction resistances so that the rotation frame 1 can be freely rotated. Another exemplary embodiment utilizes a non-contact brake system comprised of coils and magnets facing the rotation frame in order to prevent the problems of the friction plate 21 and the brake pad 22 wearing due to contact.

Figure 9:
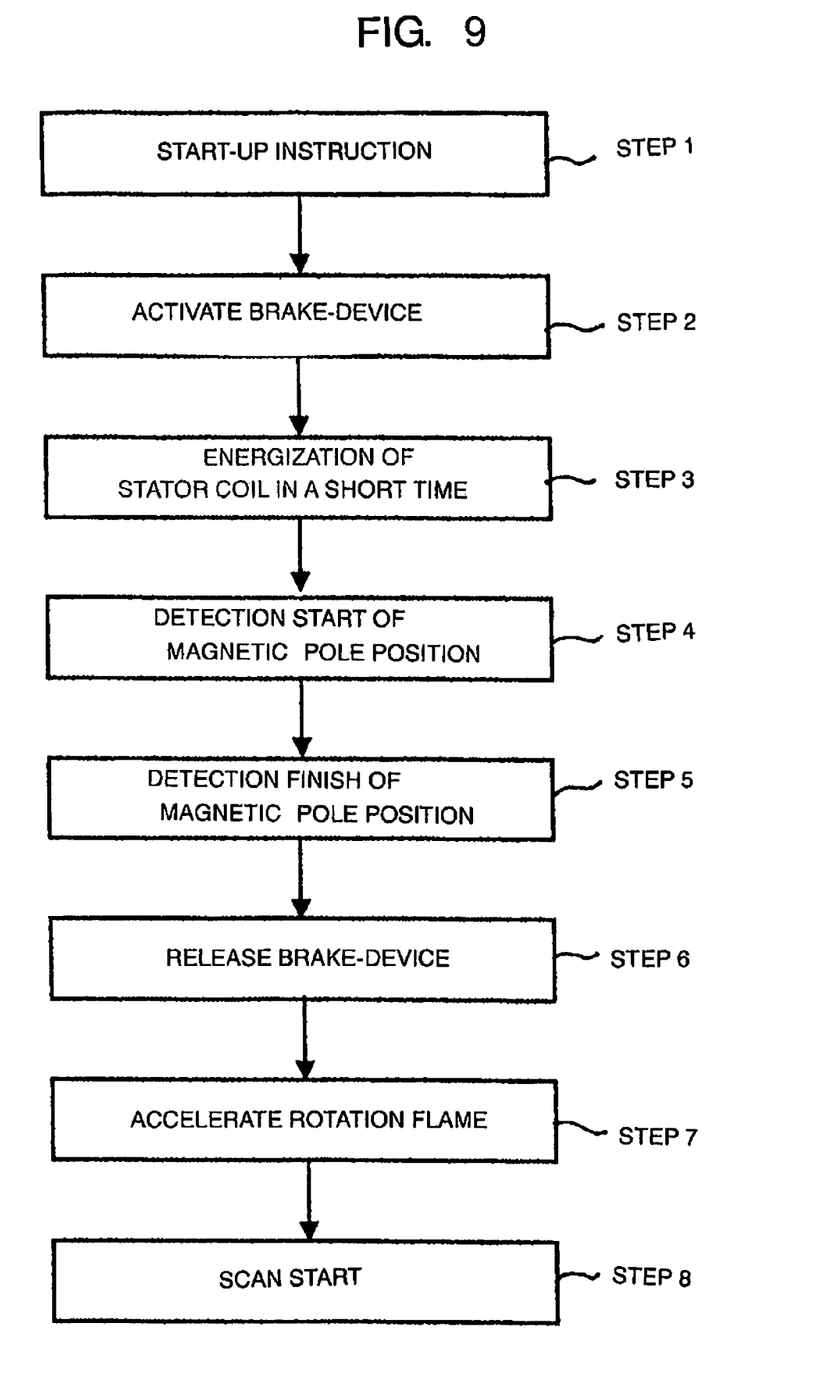
FIG. 9 is a flowchart illustrating an automatic detecting operation of a magnetic pole for rotating a gantry in an X-ray CT apparatus consistent with the embodiment of FIG. 1.

FIG. 9 is a flowchart illustrating an automatic magnetic pole detecting method for a gantry rotation at a start-up time in an exemplary embodiment of the DD motor drive type X-ray CT apparatus consistent with the present invention. First, a user performs a prescribed operation to the CT main control unit 9 so as to instruct energizing a magnetic pole position detecting operation (FIG. 9, step 1). The CT main control unit 9 immediately activates the brake mechanism 20 so as to stop the rotation of the rotation frame 1 (FIG. 9, step 2). Upon receiving the start instruction, the servo amplifier 8 supplies driving signals to the DD motor driving circuit 14 and the DD motor driving circuit 14 supplies a driving current to the stator coil 12 during a very short time period (FIG. 9, step 3). In the case of an electromagnetic brake mechanism, a brake pad provided on the fixed gantry is pushed to a friction plate 21 provided on the rotation frame 1. In the case of a non-contact brake comprising a coil and a magnet, a magnetic force between the coil and the magnet is applied to the partial or the entire circumference of the rotation frame to prohibit the rotation.

In other exemplary embodiments, it is possible to perform the above-mentioned steps 2 and 3 in a reverse order or at the same time. Further, the order of steps 2 and 3 may be based on a start-up instruction. After activating the brake system, it is possible to apply a current to the plurality of stator coils by supplying a driving current to the DD motor driving circuit in a short time. In another exemplary embodiment, it is also possible to apply a current to the plurality of stator coils while simultaneously supplying a driving current to the DD motor driving circuit during a short time based on a start-up instruction, and then activate, by the CT control unit, the brake system to prevent rotation of the rotation frame 1.

When imperceptible vibrations of the rotation frame 1 occur due to the prohibition of the rotation by the brake system, detection of the magnetic pole position is automatically started (FIG. 9, step 4). Detection of the magnetic pole position is performed by the magnetic pole position detection unit 7 based on the number of encode pulses received from the magnetic sensor 5 between a vibration start-up time of the rotation frame 1 and a stop time of the rotation frame 1 after converging the vibration.

When the rotation frame 1 is stopped, detection of the magnetic pole position is finished (FIG. 9, step 5). The CT main control unit 9 releases the brake mechanism 20 and finishes the magnetic pole position detecting operation (FIG. 9, step 6). Consequently, because the rotation frame 1 can be freely rotated, the CT main control unit 9 accelerates the rotation speed of the rotation frame 1 up to a normal rotation speed for performing scans (FIG. 9, step 7). When the rotation speed of the rotation frame 1 reaches a prescribed constant speed, the X-ray CT apparatus starts scans to acquire projection data (FIG. 9, step 8).

In an exemplary embodiment, the brake pad 22 of the brake mechanism 20 is driven by an electromagnetic driving unit, though other embodiments may use another type of driving unit, such as a hydraulic drive, a gas-pressure drive or an air-pressure drive. Further, while the friction plate 21 is provided on a surface side of the rotation frame 1 in the exemplary embodiment described above, the friction plate 21 can be provided on a spherical surface side of the rotation frame 1. Thus, the brake pad 22 can be provided at any portion of the fixed gantry 4 so as to face the position of the friction plate 21. Further, the rotation frame 1 can be used as the friction plate 21 without attaching a special material so that the brake pad 22 directly pushes onto a surface of the rotation frame 1.

The present invention is applicable to an X-ray CT apparatus in which a rotation frame is rotated inside of a fixed gantry and to an X-ray CT apparatus in which a rotation frame is rotated outside of a fixed gantry.

The X-ray CT apparatus consistent with the embodiments of the present invention includes a DD motor driving mechanism configured to support a rotation frame on a fixed gantry by a non-contact supporting unit such as an air bearing. Accordingly, it becomes possible to easily detect a magnetic pole position at a start-up time. As a result, it becomes possible to quickly start acquisition of projection data by steadily starting up the DD motor.

While certain embodiments have been described, these embodiments are presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray CT apparatus comprising:
a fixed gantry having a plurality of stator coils arranged in a circle mounted thereon;
a ring-shaped rotation frame including a plurality of rotor magnets facing the plurality of stator coils;
an X-ray tube and an X-ray detector situated on the rotation frame so as to face each other;
a supporting unit configured to provide non-contact support of the rotation frame on the fixed gantry;
a magnetic pole detection unit configured to detect a magnetic pole position of the rotor magnet at a start-up time of the plurality of stator coils; and
a brake unit configured to apply a brake load to the rotation frame when detecting the magnetic pole position and to remove the brake load after detecting the magnetic pole position.

2. The X-ray CT apparatus according to claim 1, wherein the supporting unit supports the rotation frame on the fixed gantry through an air bearing.

3. The X-ray CT apparatus according to claim 1, wherein the brake unit comprises a friction plate on a portion of a surface of the rotation frame and a brake pad situated on the fixed gantry so as to electromagnetically be pushed in contact with the friction plate.

4. The X-ray CT apparatus according to claim 1, wherein the brake unit comprises a portion of the stator coil and a magnet apart from the surface of the rotation frame, the brake unit configured to electromagnetically operate as a non-contact brake.

5. The X-ray CT apparatus according to claim 1, wherein the brake unit comprises a brake pad driven by one of a hydraulic drive, gas-pressure drive and air-pressure drive.

6. The X-ray CT apparatus according to claim 5, wherein a current is applied to bring the brake pad into contact with the friction plate and the current is stopped to separate the brake pad from the friction plate.

7. A method for detecting a magnetic pole position of a direct drive (DD) motor type X-ray CT apparatus that includes a fixed gantry having a plurality of stator coils mounted thereon and arranged in a circle, and a ring-shaped rotation frame having a plurality of rotor magnets facing the plurality of stator coils, the method comprising:
activating a magnetic pole position detection function at a start-up time;
based on the activation of the magnetic pole position detection function, applying a current to the plurality of stator coils;
applying a brake load to the rotation frame; and
detecting a magnetic pole position of a said rotor magnet based on a number of encode pulses generated between a vibration start-up time and a vibration stop time, where the vibration starts in response to the application of the brake load.

8. The magnetic pole position detecting method according to claim 7, wherein applying the brake load to the rotation frame occurs prior to applying the current to the plurality of stator coils.

9. The magnetic pole position detecting method according to claim 7, wherein applying the current to the plurality of stator coils occurs simultaneously with applying the brake load to the rotation frame.

10. The magnetic pole position detecting method according to claim 7, comprising:
   counting the number of encode pulses;
   calculating a convergence time based on the number of encode pulses; and
   detecting the magnetic pole position using a predetermined relationship between the convergence time and the magnetic pole position.

11. The magnetic pole position detecting method according to claim 10, comprising determining excitation conditions for the DD motor based on the magnetic pole position.

12. An X-ray CT apparatus comprising:
   a fixed gantry having a plurality of stator coils mounted thereon and arranged in a circle;
   a ring-shaped rotation frame having a plurality of rotor magnets facing the plurality of stator coils;
   an X-ray tube and an X-ray detector situated on the rotation frame to face each other;
   a supporting means for providing non-contact support of the rotation frame on the fixed gantry;
   a magnetic pole detection means for detecting a magnetic pole position of one of said rotor magnets at a start-up time of the plurality of stator coils; and
   a braking means for applying a brake load to the rotation frame when detecting the magnetic pole position and for removing the brake load after detecting the magnetic pole position.

* * * * *